US011333282B2

(12) United States Patent
Mitrovic et al.

(10) Patent No.: US 11,333,282 B2
(45) Date of Patent: May 17, 2022

(54) LOCKING CONNECTOR

(71) Applicant: DIALITY INC., Irvine, CA (US)

(72) Inventors: Miroslav Mitrovic, Irvine, CA (US); Andres Dandler, Irvine, CA (US)

(73) Assignee: DIALITY INC., Irvine, CA (US)

( * ) Notice: Subject to any disclaimer, the term of this patent is extended or adjusted under 35 U.S.C. 154(b) by 209 days.

(21) Appl. No.: 16/674,427

(22) Filed: Nov. 5, 2019

(65) Prior Publication Data

US 2021/0131596 A1 May 6, 2021

(51) Int. Cl.

*F16L 37/098* (2006.01)
*F16L 37/138* (2006.01)
*F16L 13/16* (2006.01)
*F16L 37/133* (2006.01)
*F16L 33/22* (2006.01)
*F16L 13/14* (2006.01)

(52) U.S. Cl.

CPC ......... *F16L 37/0985* (2013.01); *F16L 13/146* (2013.01); *F16L 13/16* (2013.01); *F16L 33/225* (2013.01); *F16L 37/133* (2013.01); *F16L 37/138* (2013.01)

(58) Field of Classification Search

CPC . F16L 37/098; F16L 37/0985; F16L 37/0847; A61M 39/1011

See application file for complete search history.

(56) References Cited

U.S. PATENT DOCUMENTS 4,219,222 A * 8/1980 Brusadin ............. F16L 37/0985 285/8
4,429,906 A * 2/1984 Spadotto ................. F16L 37/40 285/315
4,660,803 A * 4/1987 Johnston ............ F16L 37/0985 137/533.17
4,681,350 A * 7/1987 Gaita .................. F16L 37/0985 267/182
5,029,904 A 7/1991 Hunt
5,462,313 A 10/1995 Rea et al.
5,882,047 A * 3/1999 Ostrander .............. F16L 33/22 285/319
6,199,913 B1 * 3/2001 Wang .................. F16L 37/0985 285/24
7,017,948 B2 3/2006 Sunohara et al.
7,878,552 B2 * 2/2011 Freter .................. F16L 37/098 285/308

(Continued)

FOREIGN PATENT DOCUMENTS

FR 2915553 A1 * 10/2008 ............ F16L 37/091
GB 2104607 A * 3/1983 .......... F16L 37/0985

*Primary Examiner* — Matthew Troutman
*Assistant Examiner* — Alexander T Rufrano
(74) *Attorney, Agent, or Firm* — One LLP

(57) ABSTRACT

A connector for use with a dialyzer to connect a conduit from a dialyzer with a conduit from a dialysate source. The connector includes a sleeve (female component) and a collet (male component). The sleeve has a generally cylindrical shape with an opening at one end having a circular shape with at least one slot positioned along the periphery of the circular shape. The sleeve also includes at least one flexible finger having a barb at a free end. The collet is configured to be housed within an interior chamber of the sleeve and has first and second gaps to house the barbs and first and second deflectable flanges to lock into recesses in a conduit.

17 Claims, 6 Drawing Sheets

1 10 13 22 12 14 22 24 26 52 66 74 54 60 56 70 68 72 64 58

(56) References Cited

U.S. PATENT DOCUMENTS

| | | | |
|---|---|---|---|
| 8,745,843 | B2 | 6/2014 | Michels et al. |
| 10,047,890 | B2 | 8/2018 | Li |
| 2005/0251102 | A1 | 11/2005 | Hegland et al. |
| 2007/0213690 | A1 | 9/2007 | Phillips et al. |
| 2008/0009832 | A1 | 1/2008 | Barron et al. |
| 2013/0257043 | A1 | 10/2013 | Guest |
| 2014/0264118 | A1 | 9/2014 | Tiberghien et al. |
| 2019/0107234 | A1 | 4/2019 | Corbett et al. |
| 2019/0273332 | A1 | 9/2019 | Youtsey |

* cited by examiner

LOCKING CONNECTOR

BACKGROUND OF THE INVENTION

The present invention relates to a connector that joins two conduits which transport solutions, e.g., for use with a hemodialysis system.

Applicant hereby incorporates herein by reference any and all patents and published patent applications cited or referred to in this application.

Hemodialysis is a medical procedure that is used to achieve the extracorporeal removal of waste products including creatine, urea, and free water from a patient's blood involving the diffusion of solutes across a semipermeable membrane. Failure to properly remove these waste products can result in renal failure.

During hemodialysis, the patient's blood is removed by an arterial line, treated by a dialysis machine, and returned to the body by a venous line. The dialysis machine includes a dialyzer containing a large number of hollow fibers forming a semipermeable membrane through which the blood is transported. In addition, the dialysis machine utilizes a dialysate liquid, containing the proper amounts of electrolytes and other essential constituents (such as glucose), that is also pumped through the dialyzer.

Typically, dialysate is prepared by mixing water with appropriate proportions of an acid concentrate and a bicarbonate concentrate. Preferably, the acid and the bicarbonate concentrate are separated until the final mixing right before use in the dialyzer as the calcium and magnesium in the acid concentrate will precipitate out when in contact with the high bicarbonate level in the bicarbonate concentrate. The dialysate may also include appropriate levels of sodium, potassium, chloride, and glucose.

The dialysis process across the membrane is achieved by a combination of diffusion and convection. The diffusion entails the migration of molecules by random motion from regions of high concentration to regions of low concentration. Meanwhile, convection entails the movement of solute typically in response to a difference in hydrostatic pressure. The fibers forming the semipermeable membrane separate the blood plasma from the dialysate and provide a large surface area for diffusion to take place which allows waste, including urea, potassium and phosphate, to permeate into the dialysate while preventing the transfer of larger molecules such as blood cells, polypeptides, and certain proteins into the dialysate. Typically, the dialysate flows in the opposite direction to blood flow in the extracorporeal circuit. The countercurrent flow maintains the concentration gradient across the semipermeable membrane so as to increase the efficiency of the dialysis.

Connectors are integral parts of most medical device machines. The connectors used in many medical devices, such as hemodialysis machines, are often reusable. Reusable components used in medical devices present numerous problems, including a risk of cross-contamination, infections, and healthcare-associated infections (HAIs). Reusable components and devices are designed and built to last indefinitely, assuming they are properly maintained and cleaned. Even if decontaminated properly, however, reusable devices can still lead to infection. There are also many possible harmful effects from the disinfectant chemicals being used. For example, formaldehyde, which is a commonly used disinfectant, is a known carcinogen. It can also cause severe allergic reactions, liver damage, anemia, CNS disorders, destruction of red blood cells, reproductive disorders, and kidney transplant rejection.

These risks are lower in single-use components and devices, which are sterilized and individually packaged. This reduces the spread of infection. Moreover, single use components and devices are usually associated with lower costs and increased efficiency. Single-use components and devices are designed to have less-demanding durability requirements. This allows for more cost-effective, mass production techniques.

Accordingly, there is a significant need for single-use connectors, e.g., connectors that permanently lock and cannot be released through external access, e.g., with a tool or a user's finger, for use with hemodialysis systems.

SUMMARY OF THE INVENTION

According to a first aspect of the invention, a hemodialysis system is provided including an arterial blood line for connecting to a patient's artery for collecting blood from a patient, a venous blood line for connecting to a patient's vein for returning blood to a patient, a reusable dialysis machine and a disposable dialyzer with a disposable connector(s) for joining the conduits between the dialyzer and the dialysate solutions.

The arterial blood line and venous blood line may be typical constructions known to those skilled in the art. For example, the arterial blood line may be traditional flexible hollow tubing connected to a needle for collecting blood from a patient's artery. Similarly, the venous blood line may be a traditional flexible tube and needle for returning blood to a patient's vein. Various constructions and surgical procedures may be employed to gain access to a patient's blood including an intravenous catheter, an arteriovenous fistula, or a synthetic graft.

Preferably, the disposable dialyzer has a construction and design known to those skilled in the art including a blood flow path and a dialysate flow path. The term "flow path" is intended to refer to one or more fluid conduits, also referred to as passageways, for transporting fluids. The conduits may be constructed in any manner as can be determined by ones skilled in the art, such as including flexible medical tubing or non-flexible hollow metal or plastic housings. The blood flow path transports blood in a closed loop system by connecting to the arterial blood line and venous blood line for transporting blood from a patient to the dialyzer and back to the patient. Meanwhile, the dialysate flow path transports dialysate in a closed loop system from a supply of dialysate through a connector to the dialyzer and back through a connector to the dialysate supply. Both the blood flow path and the dialysate flow path pass through the dialyzer, but are separated by the dialyzer's semipermeable membrane.

In one embodiment, the disclosure provides a connector to receive and join first and second conduits, the connector comprising: a sleeve comprising an elongate tubular body having an interior chamber, a first opening at a first end, a second opening at a second end, and at least one flexible finger having a barb at a free end, wherein the first opening comprises a substantially circular shape with at least one slot positioned along the periphery of the circular shape, and wherein the at least one flexible finger is attached to the first end at the first slot and extends into the interior chamber; a collet configured to be housed within the interior chamber of the sleeve, the collet comprising first and second cylindrical bodies each having a first end and a second end, the first end of the second cylindrical body joining the second end of the first cylindrical body to form a shoulder, at least one ridge extending along a longitudinal axis on an outer surface of the first cylindrical body, a collar disposed along the outer surface of the first cylindrical body between the at least one ridge and the shoulder, a first gap formed between the at least one ridge and the collar and a second gap formed between the collar and the shoulder, and first and second deflectable flanges located in a region near the second end of the second cylindrical body and having a first and a second surface or circumferential ridge on an interior side of the first and second flanges, respectively, wherein the first end of the first cylindrical body is configured to pass through the first opening of the sleeve, such that the at least one ridge passes through the at least one slot, wherein an end of the first conduit is configured to pass through the opening of the first cylindrical body into a lumen of the first cylindrical body and wherein an end of the second conduit is configured to pass through the second end of the second cylindrical body into a lumen of the second cylindrical body, wherein in a first position, the barb is housed within the first gap, and wherein in a second position, the barb is housed within the second gap and the first and second surface or circumferential ridges are housed with a first and second recess in an outer surface of the second conduit.

In another embodiment, the first conduit transfers dialysate solution and the second conduit is an elongate tubular projection extending from a body of a dialyzer.

In another embodiment, the first opening of the sleeve further comprises an additional slot, wherein the at least one slot and the additional slot are positioned along the periphery of the circular shape approximately 180° apart. The collet may further comprise an additional ridge extending along the longitudinal axis on the outer surface of the first cylindrical body, wherein the at least one ridge and the additional ridge are positioned approximately 180° apart around the first cylindrical body, and wherein the additional ridge and the annular collar forms a third gap. The additional ridge may be configured to pass through the additional slot.

In another embodiment, the sleeve further comprises an additional flexible finger having a barb at a free end and attached to the first end at the additional slot and extends into the interior chamber. In the first position, the barb of the additional flexible finger is housed within the third gap. In the second position, the barb of the additional flexible finger is housed within the second gap.

In another embodiment, the collet further comprises an O-ring disposed within an interior chamber of the second cylindrical body near the shoulder. In the second position, the end of the second conduit resides within a lumen of the O-ring.

In another embodiment, the sleeve further comprises first and second recesses on a surface of the interior chamber, and wherein at least a portion of the first and second deflectable flanges are housed within the first and second recesses when in the second position.

In another embodiment, the sleeve further comprises first and second projections located between the first and second recesses and the first end of the sleeve, wherein the second cylindrical body further comprises first and second recesses located on an outer surface between the first and second deflectable flanges and the shoulder. The first and second projections may be housed within the first and second recesses located on an outer surface of the second cylindrical body when in the second position.

In another embodiment, the when in the second position, the barb cannot be removed from the second gap by external access, e.g., with a tool or with the user's finger. The barb is permanently housed within the second gap and the first and second surface or circumferential ridges are permanently housed with the first and second recess in the outer surface of the second conduit in the second position.

DETAILED DESCRIPTION OF THE INVENTION

Figure 1:
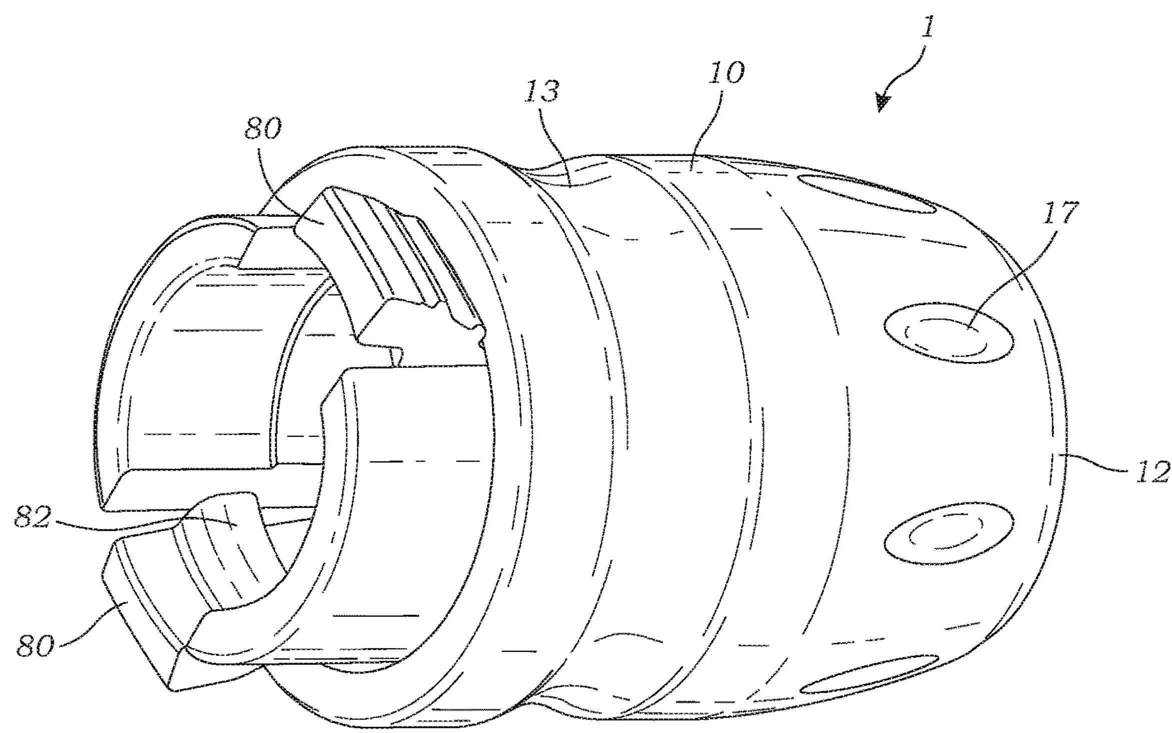
FIG. 1 is a perspective view of one embodiment of a connector according to the invention in the unlocked position.
Figure 2:
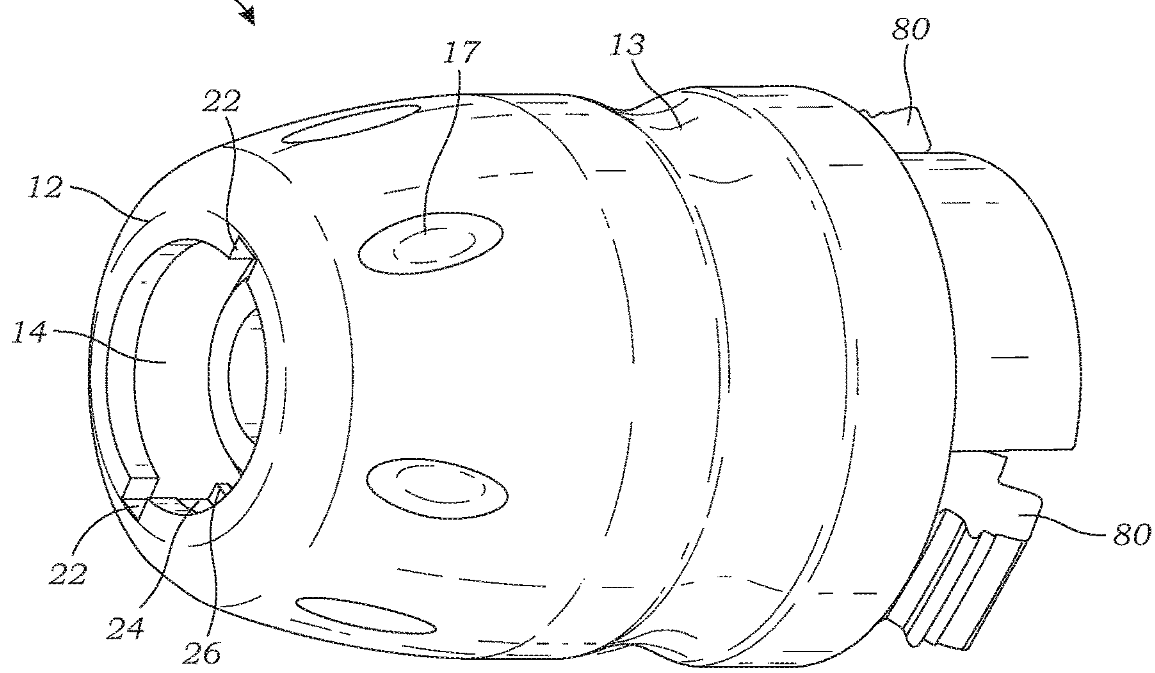
FIG. 2 is a perspective view of one embodiment of a connector according to the invention in the unlocked position.

While the present invention is capable of embodiments in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

A portion of a hemodialysis system is depicted in FIGS. 5, 8, 11, and 14. The hemodialysis system includes dialyzer 25 that is connected to both a blood flow path and a dialysate flow path. Both the blood flow path and dialysate flow path travel through dialyzer 25 to transport their respective fluids through closed loop systems wherein the dialysate flow path is isolated from the blood flow path by a semipermeable membrane (not shown). Preferably, the dialysate flows in the opposite direction to blood flow within dialyzer 25, which possesses an inlet 31 for receiving dialysate, an outlet (not shown) for expelling dialysate, an inlet (not shown) for receiving blood from a patient, and an outlet 39 for returning blood to a patient. The blood flow path and dialysate flow path are conduits. The conduits may have an inside diameter of approximately 0.156 inch (3-5 millimeters). Both the blood flow path and the dialysate flow path pass through dialyzer 25, but are separated by the dialyzer's semipermeable membrane. Dialyzer 25 is of a construction and design known to those skilled in the art. Preferably, dialyzer 25 includes a large number of hollow fibers which form a semipermeable membrane. Suitable dialyzers can be obtained from Fresenius Medical Care, Baxter International, Inc., and Nipro Medical Corporation.

Figure 3:
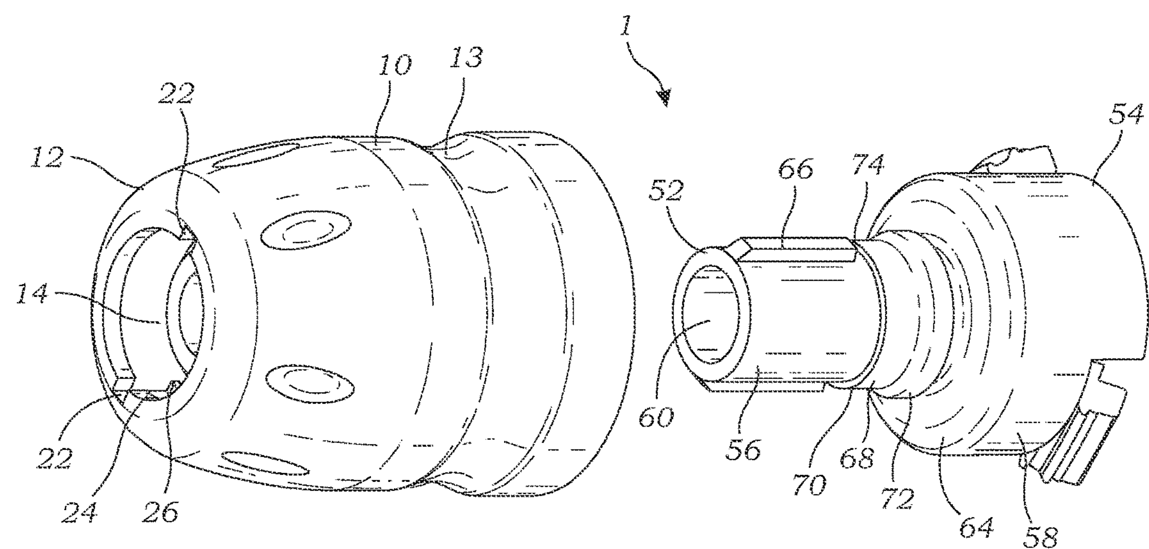
FIG. 3 is a perspective view of one embodiment of a connector according to the invention, showing a sleeve and a collet in an exploded view.
Figure 4:
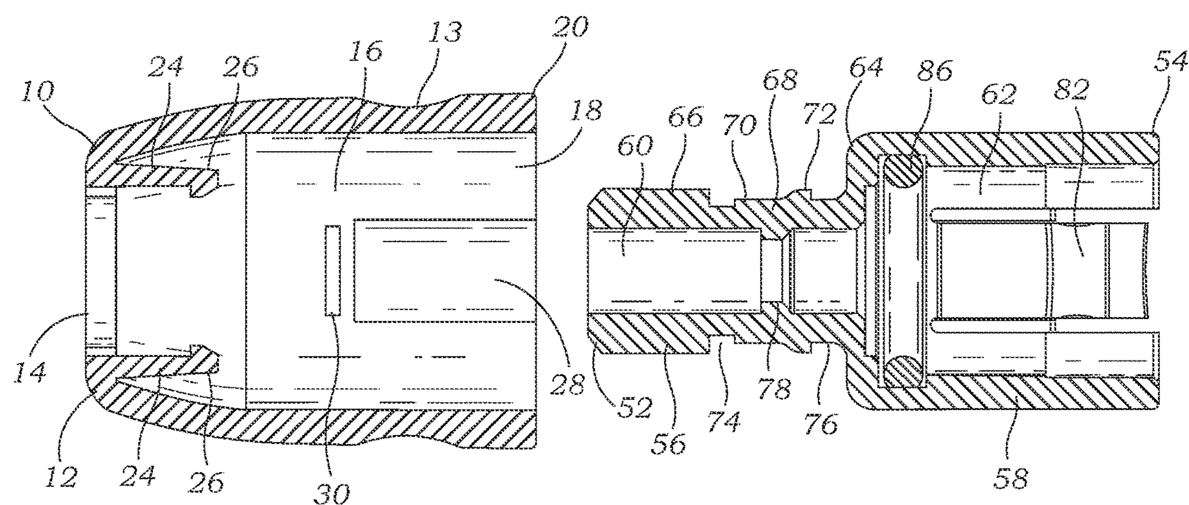
FIG. 4 is a cross-sectional view of one embodiment of a connector according to the invention, showing a sleeve and a collet in an exploded view.

As seen in FIGS. 1-7, locking connector 1 that joins a first conduit or solution transferring line 3, such as a dialysis solution circulating hose, to second conduit, such as an inlet 31 or outlet (not shown) of dialyzer 25 is described. As seen in FIGS. 1-4, connector 1 comprises female element or sleeve 10. Sleeve 10 is an elongate tubular body having an opening 14 at first end 12, and lumen or interior chamber 16 communicating with opening 14 at first end 12 and opening 18 at second end 20. An outer surface of sleeve 10 may have annular recess 13 to assist a user with gripping connector 1. Recesses 17 situated on the outer surface of sleeve 10 may also assist the user with gripping connector 1. Opening 14 at first end 12 is configured to receive an end portion of a fluid-flow conduit 3 and has a substantially circular shape with two slots 22 along the periphery of the circle arranged approximately 180° apart in the circle. Sleeve 10 also includes two flexible fingers 24 that extend into lumen 16 of sleeve 10 from the edge of slots 22 located along the perimeter of the circular opening 14 at first end 12, the two flexible fingers 24 including enlarged free ends or barbs 26. The interior chamber of sleeve 10 defining lumen 16 is substantially cylindrical, tapering slightly towards first end 12, such that the diameter of lumen 16 at second end 20 is larger than the diameter of lumen 16 at first end 12. Sleeve 10 has a substantially circular opening 18 at second end 20 through which a male component or collet 50 is received. As seen in FIG. 4, the interior surface of sleeve 10 include two indentations or recesses 28 in the region at second end 20 of sleeve 10 that are arranged approximately 180° apart in the circle defined by the sleeve. The two indentations or recesses 28 are also arranged such that they are each offset by approximately 90° from flexible fingers 24 at first end 12. Sleeve 10 also includes first and second projections 30 located directly above each indentation, such that the projections are also arranged so that they are each offset by approximately 90° from flexible fingers 24 at first end 12.

As seen in FIGS. 1-4, connector 1 also includes a male component or collet 50 that is configured to be received in interior chamber 16 of sleeve 10. Collet 50 has first and second ends 52, 54 and includes first and second cylindrical bodies 56, 58, each having a lumen 60, 62, respectively. Lumen 60 of first cylindrical body 56 communicates with lumen 62 of second cylindrical body 58. First cylindrical body 56 has a smaller diameter (both inner and outer) than second cylindrical body 58 and terminates at first end 52 of collet 50. Collet 50 has a shoulder or shelf 64 where second cylindrical body 58 meets, joins, or connects to first cylindrical body 56. Collet 50 has an outer surface of first cylindrical body 56 that includes posts or ridges 66 extending along a longitudinal axis of the first cylindrical body and collar 68 that forms first and second annular ridges 70, 72, first annular ridge 70 being closer to first end 52 of collet 50 than second annular ridge 72. First annular ridge 70 may be smaller than second annular ridge 72. Posts or ridges 66 extend from first end 52 of collet 50 down along a longitudinal axis of first cylindrical body 56, approximately about half (½) of the length of the first cylindrical body, alternatively about one-third (⅓), alternatively about two-thirds (⅔), alternatively about three-fourths (¾) of the length of first cylindrical body 56, and terminate before first annular ridge 70 of collar 68. The ends of each of the posts or ridges 66 and the first annular ridge 70 form first and second gaps 74 that are configured to hold enlarged ends or barbs 26 of the flexible fingers 24. The second annular ridge 72 of collar 68 and shoulder or shelf 64 forms an annular gap 76 that is also configured to hold enlarged ends or barbs 26 of the flexible fingers 24.

Figure 9:
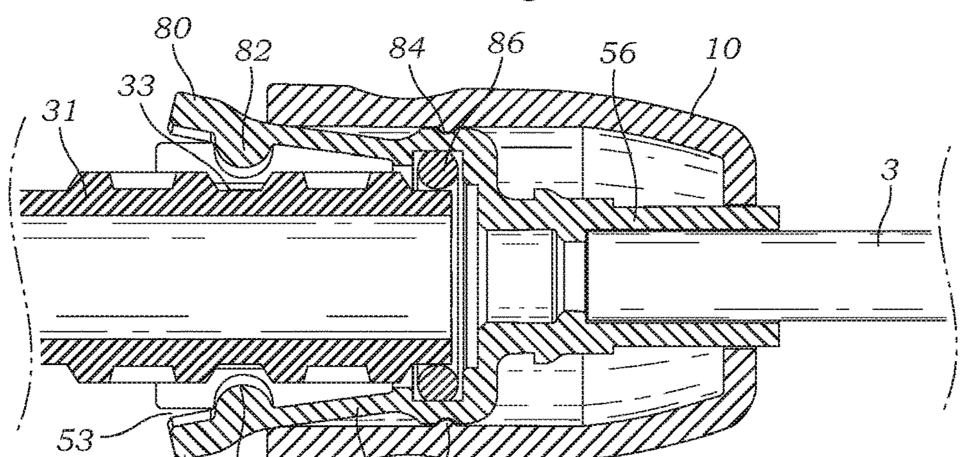
FIG. 9 is a cross-sectional view of the portion of the dialyzer inserted into one embodiment of a connector according to the invention.

As seen in FIG. 4, the interior of first cylindrical body 56 includes annular ridge 78 that lies on the interior surface of the first cylindrical body, positioned between the first and second annular ridges 70, 72 located on the outside of first cylindrical body 56. Second cylindrical body 58 has first and second flexible, deflecting or deflectable flanges 80 in the region near second end 54 of collet 50. Flanges 80 include ribs 82 running along a horizontal axis of flange 80 that are configured to lock into an opening, recess, or gap 33 in the outer surface of the inlet (e.g., from the dialyzer) to be connected. As seen in FIG. 3 and FIG. 9, the outer surface of second cylindrical body 58 also includes first and second recesses 84 above flanges 80, located between flanges 80 and the shoulder or shelf 64, that are configured to house projections 30 in the interior of sleeve 10. The outer diameter of first cylindrical body 56 is slightly smaller than the diameter of opening 14 of sleeve 10 at first end 12, such that first cylindrical body 56 is configured to pass through opening 14 of sleeve 10 at first end 12, and posts or ridges 66 on the outside surface of first cylindrical body 56 pass through slots 22 in opening 14 at first end 12 of sleeve 10. An O-ring 86 is seated in annular groove 88 in the lumen 62 of second cylindrical body 58 adjacent to shelf or shoulder 64 (see FIG. 4).

Figure 5:
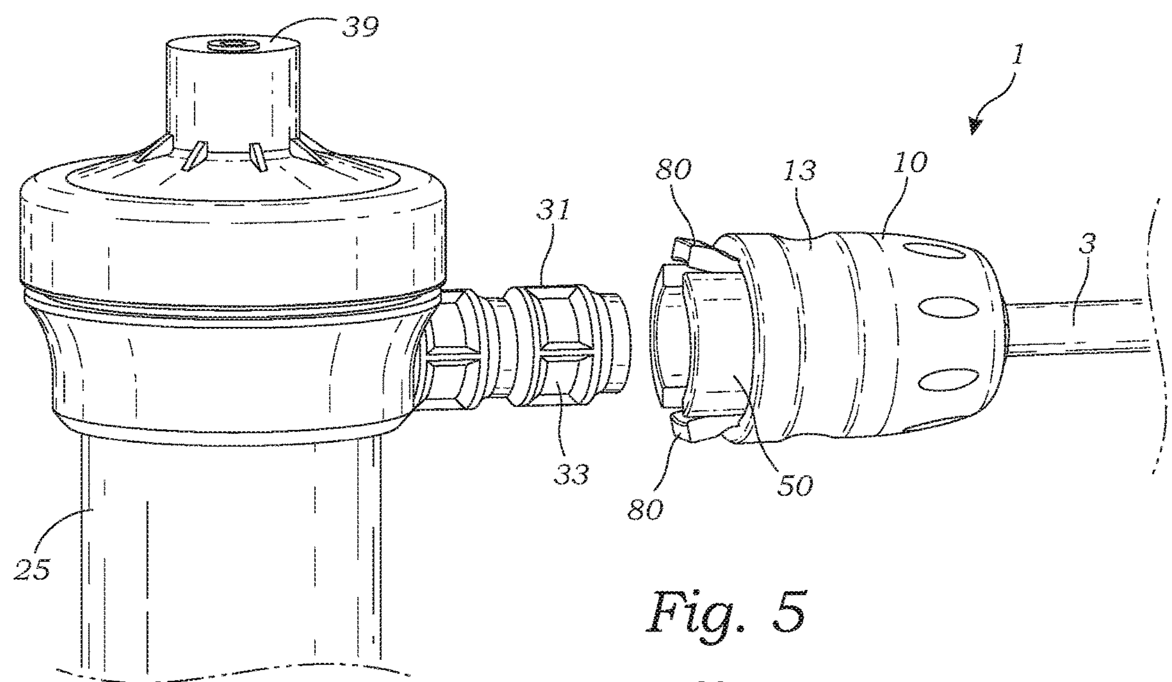
FIG. 5 is a perspective view of one embodiment of a connector and a portion of a dialyzer before they are connected.
Figure 6:
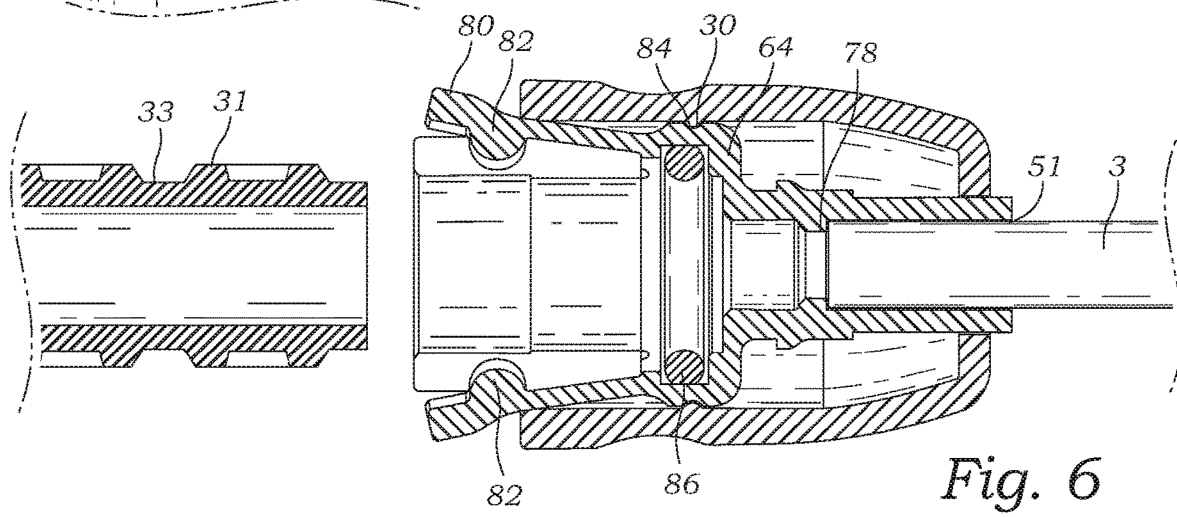
FIG. 6 is a cross-sectional view of one embodiment of a connector according to the invention before they are connected.
Figure 7:
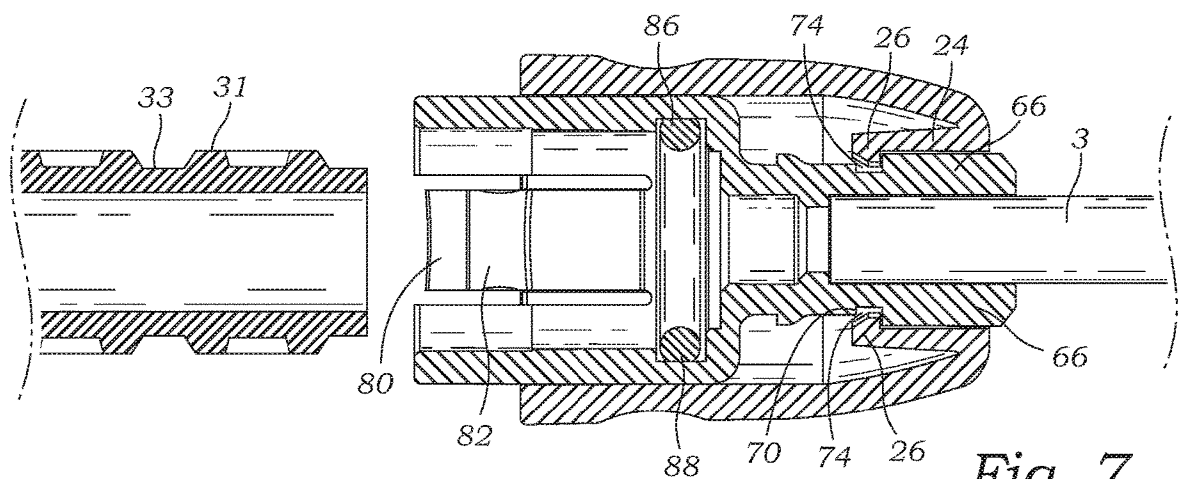
FIG. 7 is a cross-sectional view of one embodiment of the connector depicted in FIG. 6, rotated 90°.

FIGS. 5-7 show sleeve 10 with fluid-flow conduit 3, e.g. dialysis tubing, inserted into opening 14 at first end 12 of sleeve 10 and through opening 51 in first end 52 of collet 50 such that tubing 3 resides in lumen 60 of first cylindrical body 56 and abuts the annular ridge 78 in the interior of first cylindrical body 56. Collet 50 is inserted through opening 18 in second end 20 of sleeve 10 and resides in interior chamber 16. As seen in FIG. 6, with respect to sleeve 10, collet 50 is oriented such that deflectable flanges 80 are residing within indentations or recesses 28 in the interior surface of sleeve 10 and projections 30 above indentations 28 are housed within first and second recesses 84 in the outer surface of the second cylindrical body near the shoulder or shelf. As seen in FIG. 7, which shows the connector rotated 90° from the view in FIG. 6, barbs or enlarged ends 26 of the flexible fingers 24 reside in first and second gaps 74 formed between the ends of each of the or ridges 66 and first annular ridge 70, thereby temporarily locking collet 50 in a first position in the interior chamber of sleeve 10.

Figure 8:
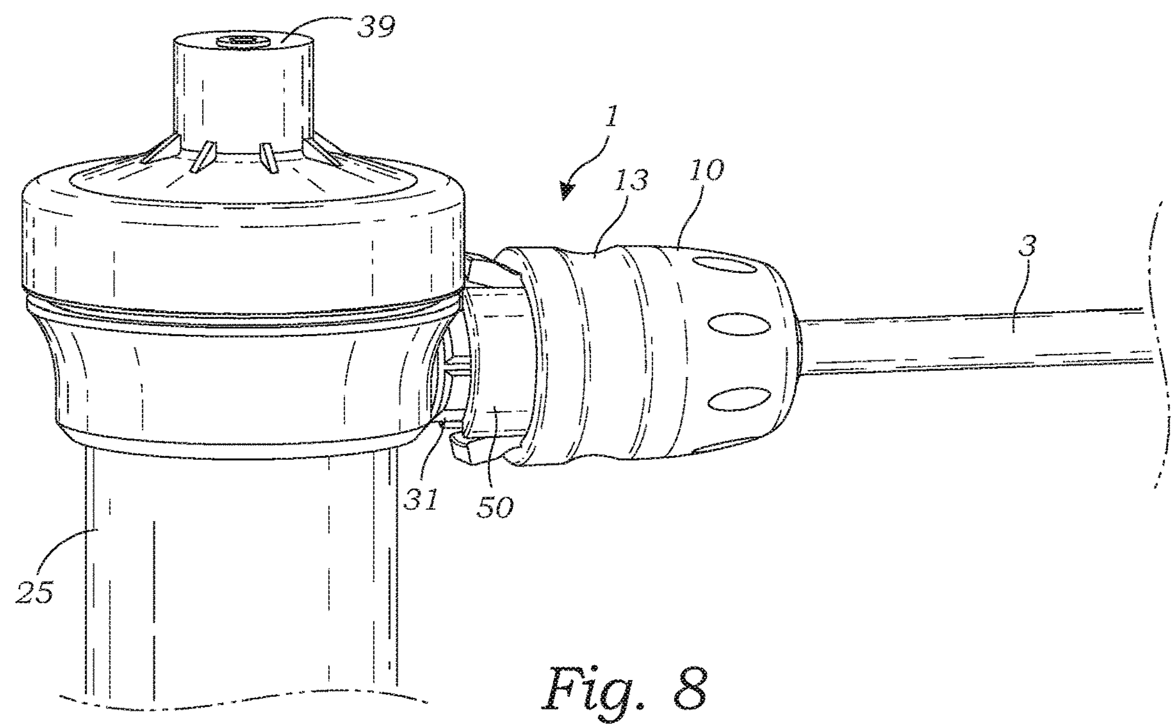
FIG. 8 is a perspective view of a portion of a dialyzer inserted into one embodiment of a connector according to the invention.
Figure 10:
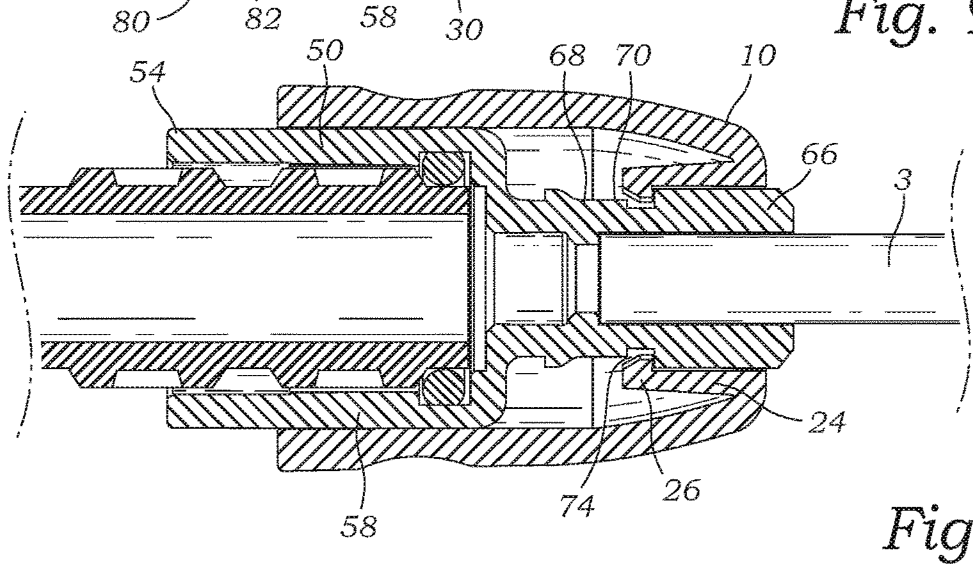
FIG. 10 is a cross-sectional view of the portion of the dialyzer and one embodiment of the connector depicted in FIG. 9, rotated 90°.

As seen in FIGS. 8-10, inlet 31 (or outlet, not shown) is inserted through opening 53 at second end 54 of collet 50 such that a distal region of inlet 31 (or outlet) is housed within the lumen 62 or interior chamber of second cylindrical body 58. Inlet 31 (or outlet) is inserted into lumen 62 of second cylindrical body 58 and advanced until the end abuts shoulder or shelf 64 and resides within the lumen of O-ring 86. Surface or circumferential ridges 82 of deflectable flanges 80 are adjacent the gaps or recesses 33 in the outer surface of the inlet 31 (or outlet), but the deflectable flanges 80 are still extending radially outward such that surface or circumferential ridges 82 are not locked into the gaps or recesses 33 of inlet 31 (or outlet). As seen in FIGS. 9 and 10, which is a 90° rotation of the view in FIG. 9, collet 50 is still in the first position in the interior chamber 16 of sleeve 10, i.e., barbs or enlarged ends 26 of flexible fingers 24 still reside in first and second gaps 74 formed between the ends of each of the or ridges 66 and the first annular ridge 70 of collar 68, and projections 30 above indentations 28 are housed within first and second recesses 84 in the outer surface of the second cylindrical body near the shoulder or shelf.

Figure 11:
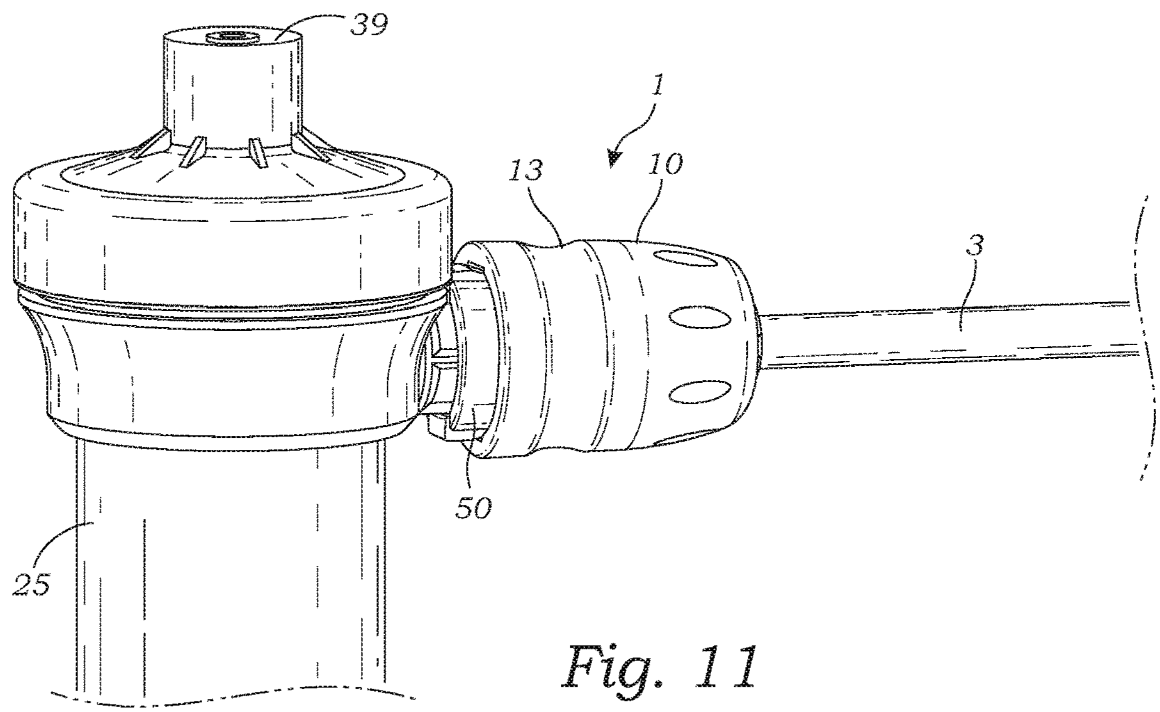
FIG. 11 is a perspective view of a portion of a dialyzer inserted into one embodiment of a connector according to the invention.
Figure 12:
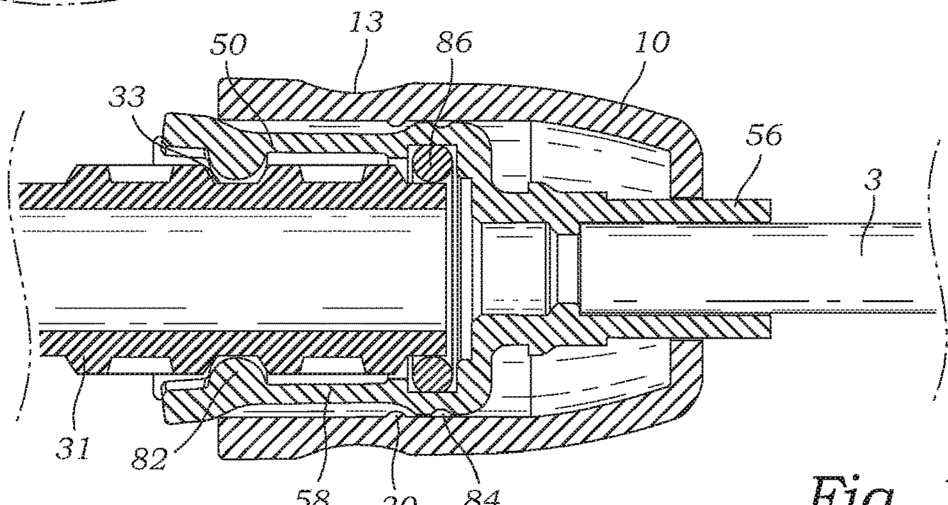
FIG. 12 is a cross-sectional view of the portion of the dialyzer inserted into one embodiment of a connector according to the invention.
Figure 13:
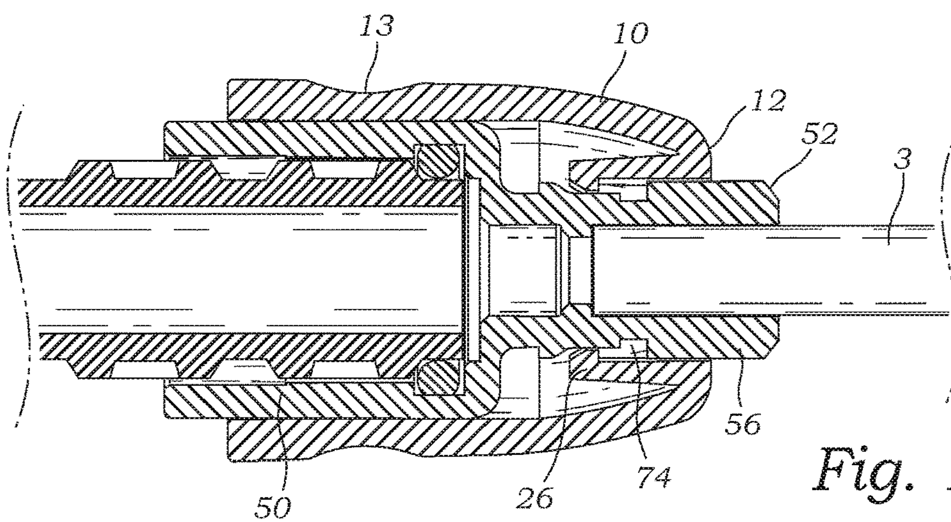
FIG. 13 is a cross-sectional view of the portion of the dialyzer inserted into one embodiment of the connector depicted in FIG. 12, rotated 90°.

As seen in FIGS. 11-13, collet 50, with inlet 31 disposed within interior chamber 62 of second cylindrical body 28, has been advanced further in the direction of first end 12 of sleeve 10, such that first end 52 of first cylindrical body 56 is moved farther past first end 12 of sleeve 10. The advancement of collet 50 forces barbs 26 out of gaps 74 and projections 30 out of first and second recesses 84 in the outside surface of second cylindrical body 58. Moreover, pressure from the interior surface of sleeve 10 forces surface or circumferential ridges 82 on the deflectable flanges 80 to be housed within gaps or recesses 33 in the outer surface of inlet 31 (or outlet).

Figure 14:
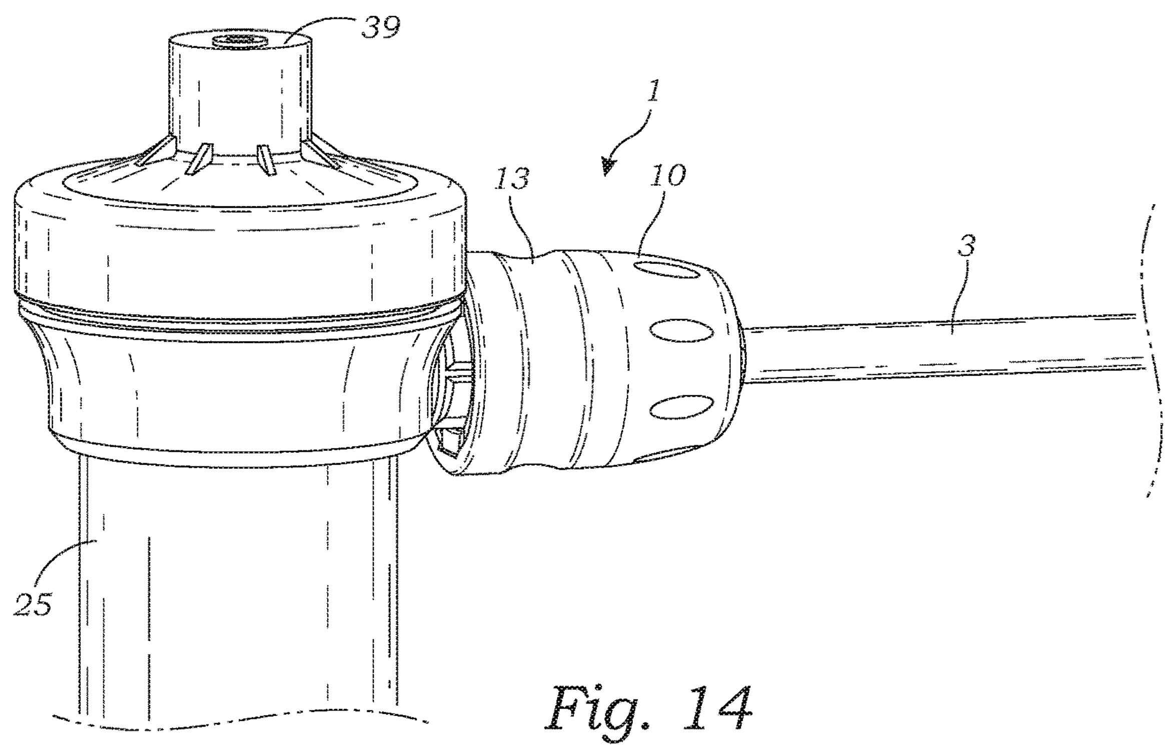
FIG. 14 is a perspective view of a portion of a dialyzer inserted into one embodiment of a connector according to the invention in a locked position.
Figure 15:
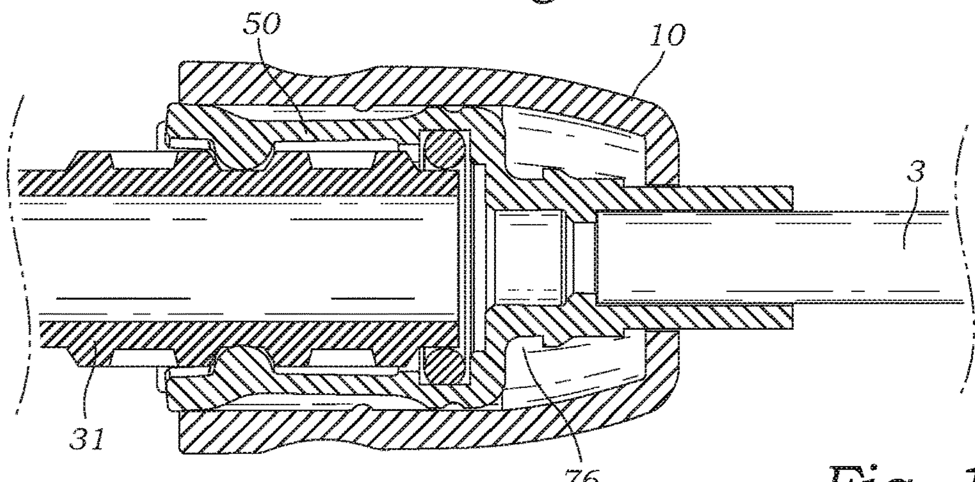
FIG. 15 is a cross-sectional view the portion of the dialyzer inserted into one embodiment of a connector according to the invention in a locked position.
Figure 16:
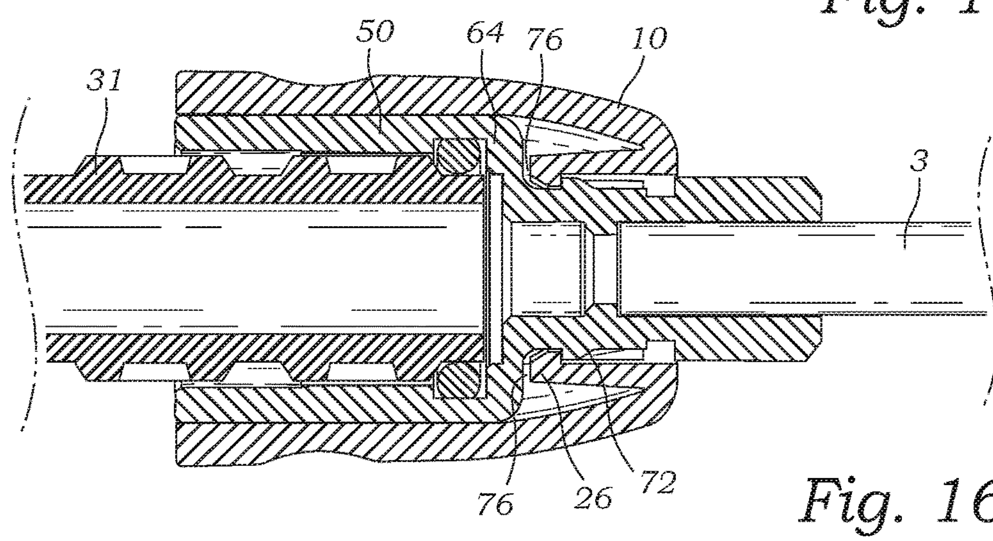
FIG. 16 is a cross-sectional view of the portion of the dialyzer and one embodiment of the connector depicted in FIG. 15, rotated 90°.

As seen in FIGS. 14-16, further advancement of collet 50 in the direction of first end 12 of sleeve 10 forces barbs 26 of flexible fingers 24 into the annular gap 76 between second annular ridge 72 and shoulder or shelf 64. This results in collet 50 being permanently locked to sleeve 10, thereby permanently connecting the dialyzer inlet 31 (or outlet) to the fluid-flow conduit 3 (e.g., dialysate tubing). Sleeve 10 does not contain any external access point such that the user could release barbs 26 of flexible fingers 24 from annular gap 76 with, e.g., a finger or a tool.

In closing, regarding the exemplary embodiments of the present invention as shown and described herein, it will be appreciated that a hemodialysis system is disclosed. The principles of the invention may be practiced in a number of configurations beyond those shown and described, so it is to be understood that the invention is not in any way limited by the exemplary embodiments, but is generally directed to a hemodialysis system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the Specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present Specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

It should be understood that the processes, methods, and the order in which the respective elements of each method are performed are purely exemplary. Depending on the implementation, they may be performed in any order or in parallel, unless indicated otherwise in the present disclosure.

While several particular forms of the invention have been illustrated and described, it will be apparent that various modifications can be made without departing from the spirit and scope of the invention. Therefore, it is not intended that the invention be limited except by the following claims.

What is claimed is:

1. A connector to receive and join first and second conduits, the connector comprising:

a sleeve comprising an elongate tubular body having an interior chamber, a first opening at a first end, a second opening at a second end, and at least one flexible finger having a barb at a free end, wherein the first opening comprises a substantially circular shape with at least one slot positioned along the periphery of the circular shape, and wherein the at least one flexible finger is attached to the first end at the first slot and extends into the interior chamber;

a collet configured to be housed within the interior chamber of the sleeve, the collet comprising first and second cylindrical bodies each having a first end and a second end, the first end of the second cylindrical body joining the second end of the first cylindrical body to form a shoulder, at least one ridge extending along a longitudinal axis on an outer surface of the first cylindrical body, a collar disposed along the outer surface of the first cylindrical body between the at least one ridge and the shoulder, a first gap formed between the at least one ridge and the collar and a second gap formed between the collar and the shoulder, and first and second deflectable flanges located in a region near the second end of the second cylindrical body and having a first and a second circumferential ridge on an interior side of the first and second flanges, respectively, wherein the first end of the first cylindrical body is configured to pass through the first opening of the sleeve, such that the at least one ridge passes through the at least one slot, wherein an end of the first conduit is configured to pass through an opening of the first cylindrical body into a lumen of the first cylindrical body and wherein an end of the second conduit is configured to pass through the second end of the second cylindrical body into a lumen of the second cylindrical body, wherein in a first position, the barb is housed within the first gap, and wherein in a second position, the barb is housed within the second gap and the first and second circumferential ridges are housed with a first and second recess in an outer surface of the second conduit.

2. The connector of claim 1, wherein the first conduit transfers dialysate solution.

3. The connector of claim 1, wherein the second conduit is an elongate tubular projection extending from a body of a dialyzer.

4. The connector of claim 1, wherein the first cylindrical body has a smaller diameter than the second cylindrical body.

5. The connector of claim 1, wherein the first opening of the sleeve further comprises an additional slot, wherein the at least one slot and the additional slot are positioned along the periphery of the circular shape approximately 180° apart.

6. The connector of claim 5, wherein the collet further comprises an additional ridge extending along the longitudinal axis on the outer surface of the first cylindrical body, wherein the at least one ridge and the additional ridge are positioned approximately 180° apart around the first cylindrical body, and wherein the additional ridge and the annular collar forms a third gap.

7. The connector of claim 6, wherein the additional ridge is configured to pass through the additional slot.

8. The connector of claim 6, wherein the sleeve further comprises an additional flexible finger having a barb at a free end and attached to the first end at the additional slot and extends into the interior chamber.

9. The connector of claim 8, wherein in the first position, the barb of the additional flexible finger is housed within the third gap, and wherein in the second position, the barb of the additional flexible finger is housed within the second gap.

10. The connector of claim 1, wherein the collet further comprises an O-ring disposed within an interior chamber of the second cylindrical body near the shoulder.

11. The connector of claim 10, wherein the end of the second conduit resides within a lumen of the O-ring in the second position.

12. The connector of claim 1, wherein the sleeve further comprises first and second recesses on a surface of the interior chamber, and wherein at least a portion of the first and second deflectable flanges are housed within the first and second recesses when in the second position.

13. The connector of claim 1, wherein the sleeve further comprises first and second projections located between the first and second recesses and the first end of the sleeve, wherein the second cylindrical body further comprises first and second recesses located on an outer surface between the first and second deflectable flanges and the shoulder.

14. The connector of claim 13, wherein the first and second projections are housed within the first and second recesses located on an outer surface of the second cylindrical body when in the second position.

15. The connector of claim 1, wherein when in the second position, the barb cannot be removed from the second gap through an external access point.

16. The connector of claim 1, wherein when in the second position, the barb cannot be removed from the second gap with a tool.

17. The connector of claim 1, wherein the barb is permanently housed within the second gap and the first and second circumferential ridges are permanently housed with the first and second recess in the outer surface of the second conduit in the second position.

* * * * *